United States Patent [19]

Mulligan et al.

[11] Patent Number: 5,015,479
[45] Date of Patent: May 14, 1991

[54] SUSTAINED RELEASE CAPSULE OR TABLET FORMULATION COMPRISING A PHARMACEUTICALLY ACCEPTABLE DIHYDROPYRIDINE

[76] Inventors: Seamus Mulligan, 4 Beech Lawn, Monksland, Ireland; Randall T. Sparks, 2620 Pinebrook Dr., Gainesville, Ga.

[21] Appl. No.: 253,357

[22] Filed: Sep. 30, 1988

Related U.S. Application Data

[63] Continuation of Ser. No. 9,510, Feb. 2, 1987, abandoned.

[51] Int. Cl.$^5$ .................... A61K 9/20; A61K 37/20; A61K 9/22
[52] U.S. Cl. .................... 424/457; 424/80; 424/462; 424/463; 424/464; 424/465; 424/468; 424/469; 514/356; 514/965
[58] Field of Search ............ 424/80, 457, 462, 463, 424/464, 465, 468, 469; 514/356, 965

[56] References Cited

U.S. PATENT DOCUMENTS

| | | | |
|---|---|---|---|
| 3,065,143 | 11/1962 | Christenson et al. | 167/82 |
| 4,369,172 | 1/1983 | Schor et al. | 424/19 |
| 4,389,393 | 6/1983 | Schor et al. | 424/19 |
| 4,539,199 | 9/1985 | Orban et al. | 424/461 |
| 4,540,566 | 9/1985 | Davis et al. | 424/22 |
| 4,562,069 | 12/1985 | Hegasy et al. | 424/80 |
| 4,695,467 | 9/1987 | Uemura et al. | 514/356 |
| 4,753,801 | 6/1988 | Oren et al. | 424/80 |

FOREIGN PATENT DOCUMENTS

1184118 3/1983 Canada.
0167909 6/1985 European Pat. Off..

*Primary Examiner*—Ronald W. Griffin

[57] ABSTRACT

A sustained release capsule or tablet formulation suitable for once-daily administration comprises an adsorbate of a mixture of a pharmaceutically useful dihydropyridine and a polyvinylpyrrolidone having an average-molecular weight greater than 55,000 adsorbed on a cross-linked polyvinylpyrrolidone and blended with a polymer or mixture of polymers which gel in the presence of water, the amount of said polymer or polymers being effective to produce the desired sustained release effect.

14 Claims, No Drawings

SUSTAINED RELEASE CAPSULE OR TABLET FORMULATION COMPRISING A PHARMACEUTICALLY ACCEPTABLE DIHYDROPYRIDINE

This application is a continuation of application Ser. No. 009,510, filed Feb. 2, 1987, now abandoned.

BACKGROUND OF THE INVENTION

This invention relates to a method for the manufacture of adsorbates for use in drug delivery systems and to the adsorbates and drug formulations thereby obtained.

It is frequently desirable to delay the release of an active substance from a pharmaceutical formulation in vivo. For example, it may be desirable to delay release of the active substance within the body so that the active substance is released at a particular target site. Various coated tablets are available which are resistant to gastric juices but which are readily soluble in the higher pH environment of the small intestine. Various controlled absorption pharmaceutical formulations are also available which have a particular dissolution pattern, resulting in a controlled absorption of the active substance and, therefore, more effective medication.

The use of many active substances in therapy is complicated by solubility problems and this is especially the case with the dihydropyridine group of drugs. Drugs of the latter type such as nifedipine are very poorly soluble in aqueous media and, whilst co-precipitates thereof with certain polymers are known to improve solubility, said co-precipitates normally require a polymer to active drug ratio exceeding 3:1 in order to be effective in producing products characterised by high bioavailability with prompt peak blood levels.

Pharmaceutical formulations based on an adsorbate of a drug within a cross-linked polymer, such as crosspovidone, are also known. Furthermore, solid, rapidly absorbable medicament formulations comprising a dihydropyridine, polyvinylpyrrolidone with an average molecular weight of 15,000 to 50,000 and cross-linked insoluble polyvinylpyrrolidone are known from EP-A-0 167 09. Such formulations are rapidly absorbable and as such must be administered three or four times daily to achieve effective therapeutic levels of the active ingredient.

It is an object of the present invention to provide a sustained release capsule or tablet formulation for once daily administration wherein the bioavailability of an otherwise poorly bioavailable active substance is enhanced and effective controlled release formulations thereof can be produced.

SUMMARY OF THE INVENTION

Accordingly, the invention provides a sustained release capsule or tablet formulation suitable for once daily administration comprising an adsorbate of a mixture of 1 part by weight of a pharmaceutically useful dihydropyridine and from 0.1 to 10 parts by weight of a polyvinylpyrrolidone having an average molecular weight greater than 55,000 adsorbed on a cross-linked polyvinylpyrrolidone in a ratio of 1 part by weight of said mixture to 0.5 to 20 parts by weight of cross-linked polyvinylpyrrolidone, blended with a polymer or mixture of polymers which gel in the presence of water, the amount of said polymer or polymers being effective to produce the desired sustained release effect.

DETAILED DESCRIPTION OF THE INVENTION

The pharmaceutically useful dihydropyridines used in the present invention generally fall within the chemical formula

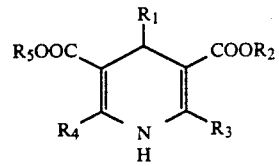

where $R_1$ is aryl or heteroaryl each of which may be substituted by various groups such as nitro and halogen whilst $R_2$, $R_3$, $R_4$ and $R_5$ which are the same or different, each represent alkyl groups which may be substituted by groups such as halogen, alkoxy, amino, alkylamino and arylalkylamino.

Preferred dihydropyridines covered by the general formula (I) are felodipine, nicardipine, nifedipine, nitrendipine, nimodipine, nisoldipine and 4-(2,1,3-benzoxadiazol-4-yl)-2,6-dimethyl-1,4-dihydro-3- isopropyloxycarbonyl-pyridine-5-carboxylic acid methyl ester.

The formation of the adsorbate may result in the dihydropyridine being in an amorphous state which can be verified by x-ray diffraction and, in addition, differential scanning calorimetry, which state is preferably retained in the sustained release formulations hereafter described.

The polyvinylpyrrolidone is preferably present in the adsorbate in an amount of 0.25-2 parts by weight relative to 1 part by weight of the dihydropyridine. Furthermore, the formulation preferably contains 1 part by weight of said mixture relative to 1-10 parts by weight of cross-linked polyvinylpyrrolidone.

The invention also provides a process for preparing a sustained release formulation as defined above, which comprises dissolving the dihydropyridine and the polyvinylpyrrolidone in a common solvent, mixing the solution thereby obtained with a given quantity of the cross-linked polyvinylpyrrolidone so as to permit adsorption of said dihydropyridine and said polyvinylpyrrolidone to said cross-linked polyvinylpyrrolidone, removing the solvent, and blending the resulting product with said polymer or mixture of polymers which gel in the presence of water and encapsulating or tabletting the resulting blend.

The solvent used is any pharmaceutically suitable co-solvent for the dihydropyridine and the polyvinylpyrrolidone.

The solvent is suitably selected from water, alcohols, ketones, halogenated aliphatic compounds, halogenated aromatic hydrocarbon compounds, aromatic hydrocarbon compounds and cyclic ethers or a mixture thereof.

Especially preferred solvents include water, hexane, heptane, methanol, ethanol, isopropyl alcohol, acetone, methylethyl ketone, methylisobutyl ketone, methylene chloride, chloroform, carbon tetrachloride, toluene, xylene and tetrahydrofuran.

Those of ordinary skill in the art will appreciate that other solvents that are effective for dissolving the dihydropyridine and the polyvinylpyrrolidone may also be used.

The polyvinylpyrrolidone is chosen to modify the dissolution of the dihydropyridine from the cross-linked polyvinylpyrrolidone and also serves to prevent any crystallisation of the dihydropyridine in the polymer matrix structure of the adsorbate during dissolution. Principally, the polyvinylpyrrolidone serves to aid the sustained release mechanism of the capsule or tablet dosage form according to the invention.

The polyvinylpyrrolidone preferably has an average molecular weight in the range 55,000 to 75,000. It is found that polyvinylpyrrolidones having a molecular weight greater than 55,000 have a viscosity which serves to sustain the release of active ingredient from the capsule or tablet formulation following administration. The greater the viscosity of the polyvinylpyrrolidone used, the slower the release of active ingredient as will be appreciated by one skilled in the art.

An especially preferred cross-linked polyvinylpyrrolidone is cross-povidone (sold under the Trade Marks Polplasdone XL (GAF) and Kollidon CL (BASF)).

For forming capsules or tablets according to the invention, the adsorbate as defined above adsorbed on the cross-linked polyvinylpyrrolidone is granulated and blended with a polymer or mixture of polymers which gels in the presence of water, and optionally other ingredients. The blend thereby obtained can be tabletted or encapsulated according to conventional methods, thereby yielding a long acting matrix system which also exhibits improved drug absorption. Suitable polymers for blending with adsorbates for subsequent tabletting or encapsulation are inert polymers, which include both water soluble and water insoluble polymers such as, for example, polyvinyl alcohol, polyvinylpyrrolidone, hydroxyethylcellulose, hydroxypropylcellulose, hydroxypropylmethylcellulose, sodium carboxymethylcellulose, alkyl-celluloses such as methyland ethylcellulose, shellac, polymers sold under the Trade Mark Eudragit, polyethylene glycol, sodium alginate, galactomannone or carboxypolymethylene or mixtures thereof.

Eudragit polymers are polymeric lacquer substances based on acrylates and/or methacrylates. Especially suitable Eudragits for use as the polymer which gels in water in the capsules or tablets according to the invention include co-polymers of acrylic and methacrylic acid esters which have varying permeability to water and active ingredient.

An especially suitable group of polymers is the polymers sold under the Trade Mark Methocel.

If one wishes to delay release of the active ingredient in vivo in capsule or tablet form, a combination of water soluble and a water insoluble polymer or a mixture of such polymers will be used, with the ratio of the water soluble to water insoluble polymer being varied to give the desired rate of release. Similarly, in the case of polymers/co-polymers of varying permeability, such as the Eudragits, the permeability characteristic of the polymers/co-polymers will be chosen to give the desired rate of release.

The adsorbates according to the present invention result in improved drug delivery relative to known active drug adsorbates in a cross-linked polymer since the adsorbates in the formulations of the present invention yield a matrix system exhibiting both delayed or sustained release of active drug and improved absorption of said active drug in vivo.

The invention will be further illustrated with reference to the following Examples.

EXAMPLE 1

Polyvinylpyrrolidone with an average molecular weight of 60,000 ( 0.75 kg) was dissolved in methylene chloride (8 kg). Nifedipine (1 kg) was then added to this solution and allowed to dissolve. The solution thereby obtained was then adsorbed onto cross-povidone (2.3 kg) and the solvent evaporated. The resulting powder was then passed through an oscillating granulator to obtain a finer particle size. X-ray diffraction and differential scanning calorimetry studies were performed on the powder and demonstrated that the nifedipine was in an amorphous form. The powder 50% was then tabletted with the following ingredients.

| Methocel K100LV (Trade Mark) | 8.0% |
| Avicel pH101 (Trade Mark) | 41.5% |
| Magnesium stearate | 0.5% | to obtain a tablet containing 20 mg of active ingredient. An x-ray diffraction pattern of the tablet was obtained which demonstrated the amorphous nature of the nifedipine had been retained.

In the above Example, the ratio of nifedipine, polyvinylpyrrolidone and cross-povidone may be altered within the limits which retain the amorphous nature of the drug. This also applies in the case of the subsequent Examples.

Furthermore, the Methocel used may be Methocel K4M, K15M, K100M, or E, J, F grades depending on the release characteristics desired.

The gel forming polymer may be used in an amount of 3–50% with proportional changes in the precentage of adsorbate used. This also applies in the case of the subsequent Examples.

EXAMPLE 2

Polyvinylpyrrolidone with an average molecular weight of 60,000 (0.65 kg) was dissolved in isopropyl alcohol (10 kg). Nicardipine (1 kg) was then added to the solution and allowed to dissolve. The solution thereby obtained was then adsorbed onto cross-povidone (3 kg) and the solvent evaporated. The resulting powder was passed through an oscillating granulator to obtain a finer particle size. The powder (60%) was then tabletted with the following ingredients:

| Methocel K100M (Trade Mark) | 8.0% |
| Avicel pH101 (Trade Mark) | 31.5% |
| Magnesium stearate | 0.5% | to obtain a tablet containing 60 mg of active ingredient.

EXAMPLE 3

The procedure of Example 1 was repeated except that the nifedipine was replaced by an equal amount (1 kg) of (4-(2,1,3-benzoxadiazol-4-yl)-2,6-dimethyl-1, 4-dihydro-3-isopropyloxycarbonyl-pyridine-5-carboxylic acid methyl ester (PN 200) and tablets containing 10 mg of active ingredient were produced.

EXAMPLE 4

Polyvinylpyrrolidone with an average molecular weight of 55,000 (0.75 kg) was dissolved in methylene chloride (12 kg) nifedipine (1. kg) was then added to this solution and allowed to dissolve The solution thereby obtained was then adsorbed onto cross-povidone (3 kg) and the solvent evaporated. The resulting powder was then passed through an oscillating granulator to obtain a fine particle size. X-ray diffraction and differential scanning calorimetry studies showed that the drug was in amorphous form in this adsorbate. The powder (30%) was then tabletted with the following ingredients:

| | |
|---|---|
| Methocel K100 LV (Trade Mark) | 10% |
| Avicel pH101 (Trade Mark) | 59.5% |
| Magnesium stearate | 0.5% | to obtain a tablet containing 20 mg active ingredient.

Similarly x-ray diffraction and differential scanning calorimetry studies show this product to be amorphous.

EXAMPLE 5

A nifedipine adsorbate was prepared as in the case of Example 4. The powder thus prepared (50%) was then blended with the following ingredients:

| | |
|---|---|
| Methocel K100 M (Trade Mark) | 44.5% |
| Avicel pH101 (Trade Mark) | 5.0% |
| Magnesium stearate | 0.5% | and encapsulating to give capsules containing 20 mg of active ingredient.

EXAMPLE 6

.8
Polyvinylpyrrolidone (1 kg) with an average molecular weight of 65,000 was dissolved in 10 kg methylene chloride. Felodipine (1.5 kg) was added and dissolved. The solution obtained was adsorbed onto cross-povidone (5 kg) and the solvent evaporated. The resulting powder was then passed through an oscillating granulator to obtain a fine particle size. X-ray diffraction and differential scanning calorimetry studies showed that the drug was in an amorphous form in this adsorbate. The powder (30%) was then tabletted with the following ingredients:

| | |
|---|---|
| Methocel K15M (Trade Mark) | 30.0% |
| Avicel pH101 (Trade Mark) | 39.5% |
| Magnesium stearate | 0.5% | to obtain a tablet containing 10 mg active ingredient.

EXAMPLE 7

Example 1 was repeated except that the adsorbate adsorbed on the cross-povidone (50%) was tabletted with

| | |
|---|---|
| Sodium alginate | 15.0% |
| Pregelatinised starch | 33.5% |
| Talc | 1.5% | to obtain tablets containing 50 mg of active ingredient.

EXAMPLE 8

Example 1 was repeated except that the adsorbate adsorbed on the cross-povidone contained nitrendipine and the final tablets contained 20 mg of the active ingredient.

EXAMPLE 9

Example 2 was repeated except that the adsorbate contained nimodipine and was tabletted with

| | |
|---|---|
| Lactose V.S.P. | 10.0% |
| Eudragit R.S. | 10.0% |
| Eudragit R.L. | 29.25% |
| Calcium stearate | 0.75% | to form tablets containing 50 mg of nimodipine.

EXAMPLE 10

Example 1 was repeated except that the adsorbate adsorbed on the cross-povidone was tabletted with

| | |
|---|---|
| Dibasic calcium phosphate dihydrate N.F. | 15.0% |
| Ethylcellulose 100 c.p.s. | 15.0% |
| Polyethyleneglycol 6000 | 5.0% |
| Hydroxyethylcellulose | 29.0% |
| Calcium stearate | 1.0% |

What we claim is:

1. A sustained release capsule or tablet formulation suitable for once daily administration comprising an adsorbate of a mixture of 1 part by weight of a pharmaceutically acceptable substantially amorphous dihydropyridine and from 0.1 to 10 parts by weight of a polyvinylpyrrolidone having an average molecular weight of at least 55,000 and having a viscosity which serves to sustain the release of active ingredients, the mixture being adsorbed on a cross-linked polyvinylpyrrolidone in a ratio of 1 part by weight of said mixture to 0.5 to 20 parts by weight of cross-linked polyvinylpyrrolidone, blended with a polymeric material which gels in the presence of water, wherein said polymeric material is selected from the group consisting of a pharmaceutically acceptable water-soluble polymer, a pharmaceutically acceptable water-insoluble polymer or mixtures of said polymers, the amount and ratio of said water-soluble polymer to said water-insoluble polymer being effective in combination with the viscosity of the polyvinylpyrrolidone to produce the desired sustained release effect.

2. A formulation according to claim 1, wherein said gel forming polymer is present in an effective amount between 3 to 50% by weight of the formulation.

3. A formulation according to claim 1, wherein the dihydropyridine falls within the formula (I)

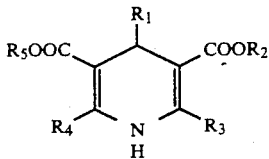

wherein $R_1$ is aryl or heteroaryl each of which is unsubstituted or substituted and $R_2$, $R_3$, $R_4$ and $R_5$, which may be the same or different, each represents an unsubstituted or substituted alkyl group.

4. A sustained release formulation according to claim 3, wherein in the dihydropyridine of the formula I, $R_1$ is aryl or heteroaryl each of which is unsubstituted or substituted by a halogen atom or a nitro group and $R_2$, $R_3$, $R_4$ and $R_5$, which may be the same or different, each represents an alkyl group unsubstituted or substituted by a halogen atom or by an alkoxy, amino, alkylamino or aralkylamino group.

5. A sustained release formulation according to claim 4, wherein the dihydropyridine is selected from the group consisting of felodipine, nicardipine, nifedipine, nitrendipine, nimodipine, nisoldipine and 4-(2,1,3-benzoxadiazol-4-yl)-2,6-dimethyl-1,4-dihydro-3-isopropyloxycarbonyl- pyridine-5-carboxylic acid methyl ester.

6. A sustained release formulation according to claim 1, wherein the polyvinylpyrrolidone is present in the adsorbate in an amount of 0.25–2 parts by weight relative to 1 part by weight of the dihydropyridine.

7. A sustained release formulation according to claim 1, which contains 1 part by weight of adsorbate relative to 1-10 parts by weight of cross-linked polyvinylpyrrolidone.

8. A sustained release formulation according to claim 1, wherein the polyvinylpyrrolidone has an average molecular weight in the range 55,000 to 75,000.

9. A sustained release formulation according to claim 1, wherein the polymer which gels in the presence of water is selected from the group consisting of polyvinyl alcohol, polyvinylpyrrolidone, hydroxyethylcellulose, hydroxypropylcellulose, hydroxypropylmethylcellulose, sodium carboxymethylcellulose, alkylcelluloses, copolymers of acrylic and methacrylic acid esters, polyethylene glycol, sodium alginate, galactomannone and carboxypolymethylene or mixtures thereof.

10. A sustained release formulation according to claim 9, wherein the polymer is hydroxypropylmethylcellulose.

11. A process for preparing a sustained release formulation according to claim 1, which comprises dissolving the dihydropyridine and the polyvinylpyrrolidone in a common solvent, mixing the solution thereby obtained with a given quantity of the cross-linked polyvinylpyrrolidone so as to permit adsorption of said dihydropyridine and said polyvinylpyrrolidone to said cross-linked polyvinylpyrrolidone, removing the solvent, and blending the resulting product with said polymer or mixture of polymers which gel in the presence of water and encapsulating or tabletting the resulting blend.

12. A process according to claim 11, wherein the solvent used is any pharmaceutically acceptable co-solvent for the dihydropyridine and the polyvinylpyrrolidone.

13. A process according to claim 12, wherein the solvent is selected from the group consisting of water, hexane, heptane, alcohols, ketones, halogenated aliphatic compounds, halogenated aromatic hydrocarbon compounds, aromatic hydrocarbon compounds and cyclic ethers or a mixture thereof.

14. A process according to claim 13, wherein the solvent is selected from the group consisting of water, hexane, heptane, methanol, ethanol, isopropyl alcohol, acetone, methylethyl ketone, methylisobutyl ketone, methylene chloride, chloroform, carbon tetrachloride, toluene, xylene and tetrahydrofuran.

* * * * *